United States Patent
Bonomi et al.

(10) Patent No.: US 10,327,651 B2
(45) Date of Patent: Jun. 25, 2019

(54) RESTING HEART RATE MONITOR SYSTEM

(71) Applicant: KONINKLIJKE PHILIPS N.V., Eindhoven (NL)

(72) Inventors: Alberto Giovanni Bonomi, Eindhoven (NL); Koen Theo Johan de Groot, Sevenum (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/316,852

(22) PCT Filed: Jun. 11, 2015

(86) PCT No.: PCT/EP2015/062995
§ 371 (c)(1),
(2) Date: Dec. 7, 2016

(87) PCT Pub. No.: WO2015/189304
PCT Pub. Date: Dec. 17, 2015

(65) Prior Publication Data
US 2017/0095159 A1  Apr. 6, 2017

(30) Foreign Application Priority Data

Jun. 12, 2014 (EP) .................... 14172096

(51) Int. Cl.
*A61B 5/024* (2006.01)
*A61B 5/11* (2006.01)
*A61B 5/00* (2006.01)

(52) U.S. Cl.
CPC .......... *A61B 5/024* (2013.01); *A61B 5/02416* (2013.01); *A61B 5/1118* (2013.01);
(Continued)

(58) Field of Classification Search
CPC ... A61B 5/024; A61B 5/1118; A61B 5/02416; A61B 5/6815; A61B 5/681; A61B 2562/0219
See application file for complete search history.

(56) References Cited

U.S. PATENT DOCUMENTS 7,753,855 B1  7/2010  Vogel et al.
2007/0249949 A1  10/2007  Hadley
(Continued)

FOREIGN PATENT DOCUMENTS

CN  1275179 C   9/2006
EP  1647227 B1  8/2008
(Continued)

OTHER PUBLICATIONS

Grant et al., "A comparison between head rate and heart rate variability as indicators of cardiac health and fitness", Frontiers in Physiology 2013, vol. 4, Article 337, pp. 1-5.
(Continued)

*Primary Examiner* — Alyssa M Alter

(57) ABSTRACT

It is an object of the present invention to provide a heart rate monitor system (10) which is able to determine the resting heart rate in an effective and unobtrusive manner. In an aspect of the present invention, a heart rate monitor system (10) comprising an inactivity determining unit (320) for determining periods of inactivity (IP) of a user based on motion data (MD) detected by at least one motion sensor (200) attached to the user and a resting heart rate calculating unit (330) for calculating a resting heart rate (RHR) of the user based on heart rate data (HR) detected by at least one heart rate sensor (100) attached to the user during the periods of inactivity (IP) as determined by the inactivity determining unit (320) is provided.

20 Claims, 3 Drawing Sheets

(52) U.S. Cl.
CPC ............ *A61B 5/681* (2013.01); *A61B 5/6815* (2013.01); *A61B 2562/0219* (2013.01)

(56) References Cited

U.S. PATENT DOCUMENTS

| | | | |
|---|---|---|---|
| 2008/0139952 A1 | 6/2008 | Kuroda et al. | |
| 2013/0209978 A1 | 8/2013 | Chen et al. | |
| 2014/0066782 A1* | 3/2014 | Addison ................ | A61B 5/024 600/476 |
| 2014/0073486 A1 | 3/2014 | Ahmed et al. | |

FOREIGN PATENT DOCUMENTS

| | | |
|---|---|---|
| JP | 2011200376 A | 10/2011 |
| WO | 2012154706 A1 | 11/2012 |
| WO | 2013068650 A2 | 5/2013 |
| WO | 2013148182 A1 | 10/2013 |
| WO | 2015066430 A1 | 5/2015 |

OTHER PUBLICATIONS

Cucherat, "Quantitative relationship between resting heart rate reduction and magnitude of clinical benefits in post-myocardial infarction: a meta-regression of randomized clinical trials", European Heart Journal 2007, vol. 28, pp. 3012-3019.

Okada et al., "Non-restrictive Heart Rate Monitoring Using an Acceleration Sensor", Proceedings of the EMBC 2006 (New York City), Aug. 30-Sep. 3, 2006, pp. 5093-5096.

Aritomo et al., "A Wrist-Mounted Activity and Pulse Recording System", Proceedings of the EMBC 1999 (Atlanta), Oct. 13-Oct. 16, 1999, p. 693.

Vrijkotte et al., "Effects of Work Stress on Ambulatory Blood Pressure, Heart Rate, and Heart Rate Variability". Hypertension, Journal of the American Heart Association (2000), vol. 35, pp. 880-886.

* cited by examiner

RESTING HEART RATE MONITOR SYSTEM

CROSS-REFERENCE TO PRIOR APPLICATIONS

This application is the U.S. National Phase application under 35 U.S.C. § 371 of International Application No. PCT/EP2015/062995, filed on Jun. 11, 2015, which claims the benefit of European Application Ser. No. 14172096.1, filed Jun. 12, 2014. These applications are hereby incorporated by reference herein, for all purposes.

FIELD OF THE INVENTION

The invention relates to a heart rate monitor system for measuring a heart rate of a user as well as a method of determining a resting heart rate of a user.

BACKGROUND OF THE INVENTION

The monitoring of a heart rate of a user for example by means of optical sensors is well known. Here, an optical sensor emits light into the skin of a user and the emitted light is scattered within the skin. Reflected light exits the skin and can be detected by an appropriate detector. Based on the received signals from the sensor, the heart rate of a user can be determined.

Heart rate sensors are for example used for fitness applications. Here, the sensors can be worn as a wrist device or as forearm device, or as a device in contact to the skin in any other location of the body. Accordingly, the heart rate sensor will detect the heart rate of the user and can display the detected heart rate on the device or to a connected system such as a display on an electronic appliance.

When the detected heart rate of a user is to be evaluated, a resting heart rate (RHR) is considered as a physiologically meaningful parameter to indicate conditions such as cardiorespiratory fitness or the like. In other words, the resting heart rate (RHR) is a very useful parameter. The resting heart rate RHR may also be used as an indication of physiological stress. Furthermore, based on the resting heart rate (RHR) and the detected heart rate of a user, the calories consumption of a user can be determined or predicted in a personalized way, thus more accurately. The resting heart rate can also be used as a predictor of the treatment effectiveness in patient's post-myocardial infarction or in patients following a rehabilitation program. The resting heart rate can also be used to evaluate the intensity of physical activities such as walking, running, cycling or the like. Here, the difference between the detected heart rate and the resting heart rate is used to determine the energy expenditure and cardio-respiratory fitness.

There are several ways to determine the resting heart rate. The resting heart rate is typically determined when a user is laying down or is at rest like in a sitting or supine position. Typically, consumption of caffeine and food is avoided and the resting heart rate is determined in the morning. This procedure is cumbersome and obtrusive as it requires refraining from eating and drinking for a sufficiently long period of time and laying down for some time in order to determine the resting heart rate.

US 2014/0066782 A1 discloses a system for determining a resting heart rate of a user. Physical signals from the user are received and monitored to identify valid heart beats. Based on the valid heart beats, a heart rate signal is determined. The heart rate signal is analyzed to identify baseline data points from the series of data points. The resting heart rate is calculated based on the base line data points.

SUMMARY OF THE INVENTION

It is an object of the present invention to provide a heart rate monitor system which is able to determine the resting heart rate in an effective and unobtrusive and non-invasive manner.

In an aspect of the present invention, a heart rate monitor system comprising an inactivity determining unit for determining periods of inactivity of a user based on motion or motion data detected by at least one motion sensor attached to the user and a resting heart rate calculating unit for calculating a resting heart rate of the user based on heart rate data measured by at least one heart rate sensor during periods of inactivity as determined by the inactivity determining unit is provided. The heart rate sensor can be attached to the user.

The heart rate monitor system comprises at least one non-invasive heart rate sensor for measuring the heart rate of the user over time and during free living condition. Hence, the heart rate sensor is measuring heart rate data of a user over a selectable period of time for example over the entire day and during free living conditions, namely non-restrictive living conditions. The heart rate monitor system comprises a reliability establishing unit for establishing or determining reliable heart rate data from among the detected heart rate data. The resting heart rate calculating unit is then able to calculate the resting heart rate of the user based on the reliable heart rate data as established by the reliability establishing unit. The reliability establishing unit is adapted to ignore heart rate data which is lower than a lower threshold or heart rate data which is above an upper threshold. Accordingly, the reliability establishing unit is performing a pre-selection of the heart rate data.

With such a heart rate monitor system, the resting heart rate of a user can be determined in an effective, non-invasive and non-obtrusive way as the user does not need to undergo any kind of restrictive protocol when the resting heart rate is to be determined. Instead, the heart rate monitor system itself will determine when the detected heart rate data can be effectively used to determine or calculate the resting heart rate. Those heart rate data are used for determining the resting heart rate which has been detected during periods of inactivity of the user.

With the help of the reliability establishing unit, those heart rate data which correspond to measurement errors or which correspond to implausible heart rate data can be excluded from the heart rate data which is used for calculating the resting heart rate. Thus, more accurate resting heart rate can be determined.

In other words, the non-invasive heart rate monitor system includes a two-step pre-selection process for the heart rate data which is used to determine the resting heart rate.

The heart rate monitor system may receive the respective motion data from the motion sensor and the respective heart rate data from heart rate sensors which do not necessarily need to be part of the heart rate monitor system. The heart rate monitor system according to this aspect of the invention only needs the motion data as well as the heart rate data to determine the resting heart rate.

According to a further aspect of the invention, the heart rate monitor system comprises at least one motion sensor for measuring or determining motion of a user over time and during free living conditions. With such a heart rate monitor system, the inactivity determining unit will determine the periods of inactivity, that means period during which the user is at rest and does not perform any major physical activity. During these periods of time, heart rate data can be measured or determined which can effectively be used to determine a resting heart rate of a user.

The reliability establishing unit is adapted to ignore heart rate data which has a standard deviation which is below a standard deviation threshold indicating poor quality in the measured heart rate data. Thus, the reliability of the heart rate data can be further increased.

According to a further aspect of the invention, the lower threshold corresponds to 30 bpm, the upper threshold corresponds to 150 bpm and the standard deviation threshold is at 0.1 bpm. With these values, the reliability establishing unit can effectively remove those heart rate data which could lead to a distortion of the resting heart rate during the calculation of the resting heart rate. These threshold values may also be modified according to the expected heart rate values for specific groups of users such as very fit individuals or patients undertaking medications.

According to a further aspect of the invention, time of day is taken into account to accept or reject heart rate data which is determined as reliable by a reliability establishing unit and in periods of inactivity as established by an inactivity determining unit. This aspect of the invention allows the system to avoid calculating resting heart rate from heart rate data captured in periods of the day for which arousing events are likely to take place according to the subjective and culturally determined habits of a user such as meals, caffeine, drugs or medications intake, or previously scheduled activities. This aspect of the invention can be integrated in the inactivity determining unit.

According to a further aspect of the invention, the inactivity determining unit can exclude those periods of inactivity that are not between 12 am and 7 pm. The period of 12 am to 7 pm is the best period during which periods of inactivity can be determined and which heart rate data is the best for calculating the resting heart rate RHR.

According to an aspect of the invention, the resting heart rate calculating unit is adapted to calculate a resting heart rate based on heart rate data over several days as well as periods of inactivity over several days.

According to a further aspect of the invention, the inactivity determining unit can exclude those periods of inactivity which follow after a physical activity. During these recovery periods, the heart rate of the user will slowly decrease such that these heart rate data should be excluded from the heart rate data which is used to calculate the resting heart rate.

According to a further aspect of the invention, a method of measuring or determining a resting heart rate of a user is provided. Periods of inactivity of a user are determined based on motion data detected by at least one motion sensor attached to the user. A resting heart rate of a user is calculated based on heart rate data detected by at least one heart rate sensor attached to the user during periods of inactivity.

According to an embodiment of the invention, a detected heart rate data as well as data regarding a motion of the user is collected over a day or several hours and are then analyzed. In particular, the measurement is performed during the normal routine of a user. The data regarding the movement of the user is analyzed to find periods of inactivity by the user. Then, the corresponding heart rate data is analyzed in order to determine a resting heart rate. The heart rate monitor system as well as the method for monitoring a heart rate according to an embodiment of the invention is advantageous. It enables an unobtrusive way to determine the resting heart rate of a user and to further monitor the heart rate of a user. In particular, the heart rate monitor system may comprise a wrist device which is used to detect the heart rate of a user as well as to detect the activity level of the user. With the heart rate monitor system according to the invention, the user can wear the monitor system during his usual daily activity while still being able to determine the resting heart rate as well as the actual heart rate.

It shall be understood that the heart rate monitor system according to claim 1, the method of determining a resting rate of a user and the computer program according to claim 11 have similar and/or identical preferred embodiments, in particular as defined in the dependent claims.

It shall be understood that a preferred embodiment in the present invention can also be any combination of the dependent claims or above embodiments with the respective independent claims.

These and other aspects of the invention will be apparent from and elucidated with reference to the embodiments described hereinafter.

DETAILED DESCRIPTION OF EMBODIMENTS

According to an aspect of the invention, a heart rate monitor system is provided which is used to measure a heart rate of a user. The heart rate monitor system can be implemented in a wrist device (like a smart watch) or other wearable devices, i.e. devices which can be attached or arranged on the skin of a user. The heart rate monitor system may comprise a heart rate sensor which can be optionally embodied as an optical sensor for determining the heart rate of a user.

The heart rate sensor according to the invention is a non-invasive heart rate sensor which is able to measure the electrical, acoustical or optical activity of the heart or the cardio-respiratory system.

Figure 1:
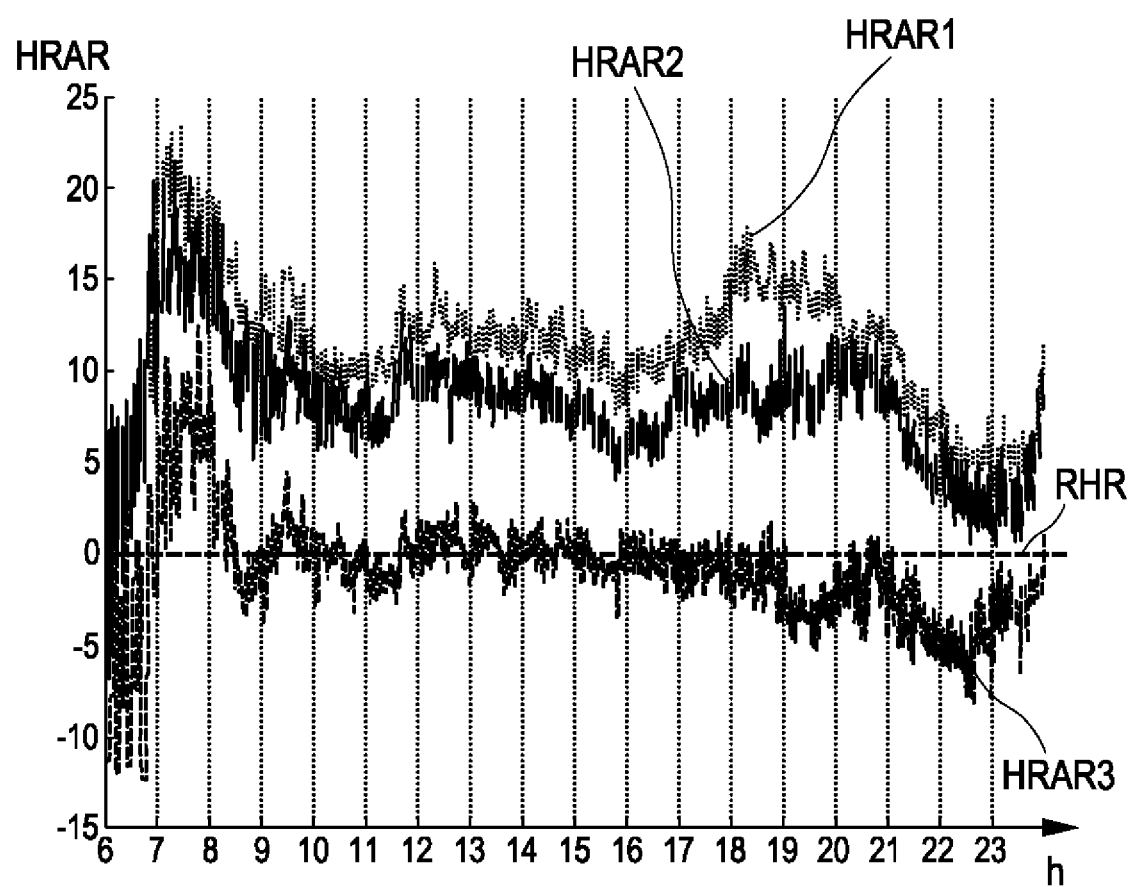
FIG. 1 shows a graph indicating a difference between a statistical representation of the detected heart rate and a resting heart rate at different times of the day in a group of subjects.

FIG. 1 shows a graph indicating a difference between a detected heart rate and a resting heart rate at different times of the day. FIG. 1 shows an example of a heart rate over time for mere illustrative purposes. On the x-axis, the hours of the day and on the y-axis, the heart rate above resting heart rate HRAR is depicted. The laboratory-determined resting heart rate RHR is shown at zero, i.e. there is no difference between the actual heart rate and the resting heart rate. The mean heart rate above resting HRAR is depicted as the line HRAR1. The median value of the heart rate above resting is depicted as line HRAR2 and the 25$^{th}$ percentile of the distribution of the heart rate above resting HRAR is depicted as line HRAR3.

As seen in FIG. 1, the mean or median heart rate value distribution over the hours of the day can lead to an overestimation of the resting heart rate. According to the invention, only those heart rate data which is detected during inactive periods of the day is advantageous in view of avoiding the above-mentioned overestimation and should thus be used. In particular as seen from line HRAR3 (the 25$^{th}$ percentile of the heart rate distribution), a good approximation in view of the resting heart rate, even during for example the time between 11 and 19 hours is shown.

In the following table 1, error statistics regarding laboratory-assessed determination of a resting heart rate RHR and any estimates of the resting heart rate from actual heart rate values recorded over the day are depicted.

TABLE 1

|  | Bias (bpm) | Root mean square error (bpm) | 95% Confidence interval (bpm) Min:Max |
|---|---|---|---|
| Whole day HR statistics | | | |
| Mean | 12.88 | 15.92 | 14.97:10.79 |
| Median | 9.15 | 12.48 | 11.04:7.256 |
| Minimum | −18.84 | 22.43 | −16.12:−21.56 |
| 25$^{th}$ percentile | 2.28 | 7.53 | 3.89:0.68 |
| Inactive minutes HR statistics | | | |
| Mean | 6.13 | 9.56 | 7.78:4.50 |
| Median | 4.02 | 8.08 | 5.58:2.46 |
| Minimum | −14.22 | 18.18 | −11.69:−16.75 |
| 25$^{th}$ percentile | −0.84 | 6.50 | 0.60:−2.3 |

Figure 2:
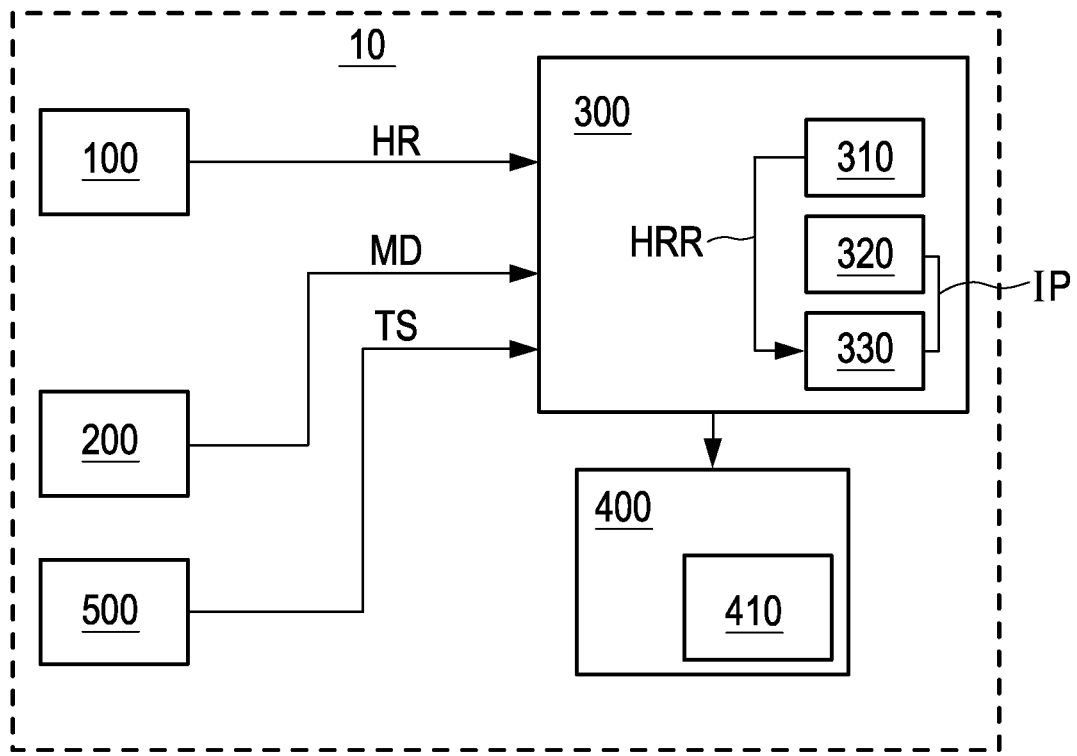
FIG. 2 shows a schematic block diagram of a heart rate monitor system according to a first embodiment.

FIG. 2 shows a schematic block diagram of a heart rate monitor system according to a first embodiment. The heart rate monitor system 10 comprises at least one non-invasive heart rate sensor 100, optionally at least one motion sensor 200 for measuring or determining motion data MD, a processing unit 300 and optionally a time stamp unit 500 and optionally a display 400. The processing unit 300 comprises optionally a reliability establishing unit 310, an inactivity determination unit 320 and a resting heart rate calculation unit 330. These three units 310, 320, 330 can be implemented as dedicated unit apart from the processing unit 300 or can be integrated or be a part of the processing unit 300. The display 400 may optionally comprise a graphic user interface GUI 410. The heart rate HR of a user is detected by the at least one non-invasive heart rate sensor 100. The heart rate data HR of the at least one non-invasive heart rate sensor 100 can comprise time stamps TS (or a time stamp can be associated to the heart rate data) which the heart rate sensor 100 can generate itself or which can be generated by a time stamp unit 500. The time stamp TS may be associated to the measurements of the heart rate sensor 100 directly in the heart rate sensor 100 or in the processing unit 300. Motion data MD of the motion sensor 200 are forwarded to the processing unit 300. The motion data MD from the motion sensor 200 can also comprise time stamp TS (or a time stamp can be associated to the heart rate data) which can be generated by the motion sensor 200 itself or by the time stamp unit 500. The time stamp TS can be incorporated into or associated to the motion data MD in the motion sensor 200 or in the processing unit 300.

In the reliability establishing unit 310, optionally the measurement data from the heart rate sensor 100, i.e. the detected heart rate HR, is analyzed to determine whether the heart rate data are reliable heart rate data HRR or whether the heart rate data is unreliable as the values thereof are too low or too high. Such unreliable values may relate to ectopic heart beats or measurement errors. Accordingly, in the reliability establishing unit 310, those data from the heart rate sensor 100 which is considered as unreliable can be removed or ignored to obtain reliable heart rate data. The detailed operation of the reliability establishing unit 310 will be described below with reference to FIG. 3.

The reliability establishing unit 320 uses a lower and upper threshold to remove unreliable data from the set of heart rate data. The upper and lower thresholds may be dependent on the heart rate sensor as used and on measurement errors. Furthermore, different threshold values may be used for children, elderly, gender-specific patients or patients undergoing medical treatment which affect the heart rate and heart rhythm of the user.

In the inactivity determining unit 310, the motion data MD from the motion sensor 200 is analyzed in order to determine periods of inactivity or resting IP. Periods of inactivity relate to periods of time during which the user refrains from physical activity, i.e. the user is resting. According to an embodiment of the invention, it is considered that periods of inactivity or rest may result in measurement data of the heart rate which could be effectively used to determine the resting heart rate RHR. Accordingly, the inactivity determining unit 320 analyses the motion data MD from the at least one motion sensor 200 as well as the time stamps TS associated to these data MD in order to determine periods of time during the day of rest or inactivity. The detailed operation of the inactivity determining unit 320 will be described below with reference to FIG. 4.

The resting heart rate calculating unit 330 can use the output data from the reliability establishing unit 310 as well as the data from the inactivity determining unit 320 to select the heart rate data from those periods of time during the day when the inactivity determining unit 320 has determined an inactivity IP or a resting of a user. In other words, only the data from the heart rate sensor 100 which corresponds to periods of time of inactivity are used to determine or calculate the resting heart rate RHR. The other heart rate data (i.e. when the user is not resting) is thus not used for the determination of the resting heart rate RHR. The detailed operation of the resting heart rate calculating unit 330 will be described below with reference to FIG. 5.

Figure 3:
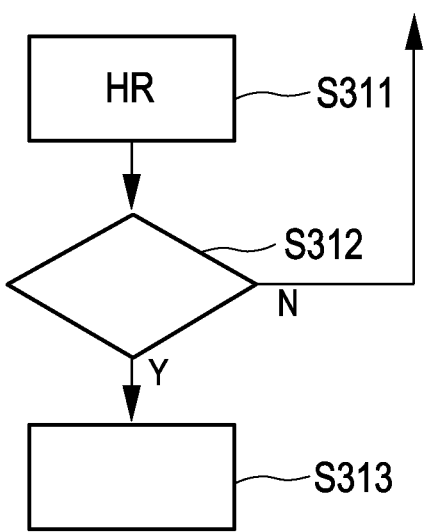
FIG. 3 shows a flow chart for determining a reliability of detected heart rate data according to an embodiment of the invention.

FIG. 3 shows a flow chart for determining a reliability of detected heart rate data according to an embodiment of the invention. In step S311, heart rate data HR from the heart rate sensor 100 is received by the reliability establishing unit S310. The heart rate data HR may also comprise a standard deviation stdHR of the heart rate HR. In step S312, the heart rate HR is compared to lower and upper thresholds. If the heart rate HR is below the lower threshold or above the upper threshold, the heart rate data is discarded and not forwarded. Furthermore, in step S312, optionally the standard deviation sdtHR of the heart rate data HR is compared to a threshold. If the standard deviation is below this threshold, the associated heart rate data is discarded or ignored. However, if the standard deviation is above the threshold value, then the corresponding heart rate data is forwarded as reliable heart rate data HRR in step S313.

According to an aspect of the invention, the lower threshold of the heart rate can be 30 bpm and the upper threshold value can for example be 150 bpm, i.e. beats per minute. The threshold for the standard deviation of the heart rate data can for example be 0.1 bpm e.g. when calculated in a time interval of for example 5 minutes in the past.

In the reliability establishing unit 310, the heart rate data HR from the heart rate sensor 100 is analyzed and only those data is forwarded which is considered to be reliable. Data which is not considered to be reliable is discarded or ignored. By introducing upper and lower threshold values for the reliable heart rate data, small or poorly reproducible heart rate data can be discarded or ignored which could otherwise lead to an inaccurate resting heart rate RHR.

Optionally, the magnitude of the heart rate data can be determined within predetermined time intervals. These time intervals can for example be 5 minutes. However, it should be noted that any other time period can also be used. Optionally, the standard deviation of the heart rate data within this time period can be determined.

Accordingly, only those heart rate data HR that are above the lower threshold (e.g. 30 bpm) and below the higher threshold (e.g. 150 bpm) and which has a standard deviation of above 0.1 bpm is determined to be or is considered as reliable heart rate data HRR.

Figure 4:
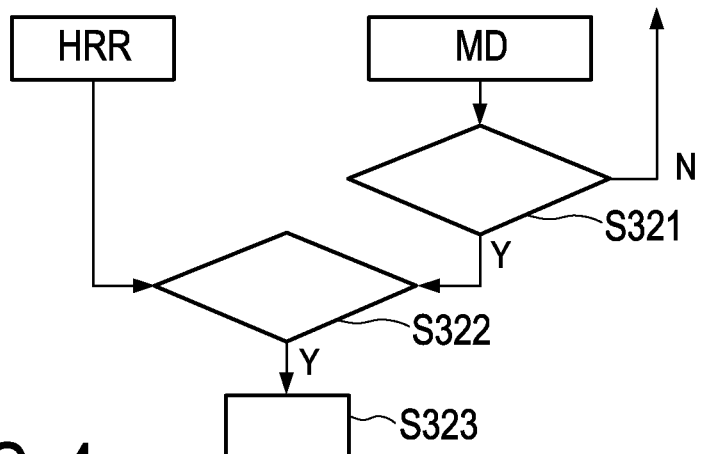
FIG. 4 shows a flow chart for determining periods of inactivity by a heart rate monitor system according to an embodiment of the invention.

FIG. 4 shows a flow chart for determining periods of inactivity by a heart rate monitor system according to an embodiment of the invention. The inactivity determining unit 320 receives the motion data MD from the at least one motion sensor 200 (as well as corresponding time stamp information TS). In step S321, the motion data MD is analyzed to determine periods of time during which no activity has taken place, i.e. in order to determine periods of inactivity or resting. Optionally, the inactivity determining unit 320 may also receive the reliable heart rate data HRR from the reliability establishing unit 310. In step S322, only those reliable heart rate data HRR is forwarded during periods of time where no motion has taken place, i.e. during periods of inactivity. In step S323, the heart rate data from the periods of inactivity can be outputted or forwarded.

The inactivity period IP can be determined by various ways based on the motion data MD from the motion sensor 200. The motion data MD may comprise activity counts, speed information, number of step information, motion level information, etc. Activity counts can for example be determined by analyzing the output of accelerometer sensors. Based on the information of periods of inactivity or resting during the day, the resting heart rate RHR can be determined. It is furthermore realized that the resting heart rate RHR can only be evaluated or determined in those periods of time where the user is inactive or is resting. The inactivity determining unit 320 can either forward information regarding periods of inactivity to the resting heart rate calculating unit 330 or it can already discard those heart rate data which originate from periods of time with increased activity.

Figure 5:
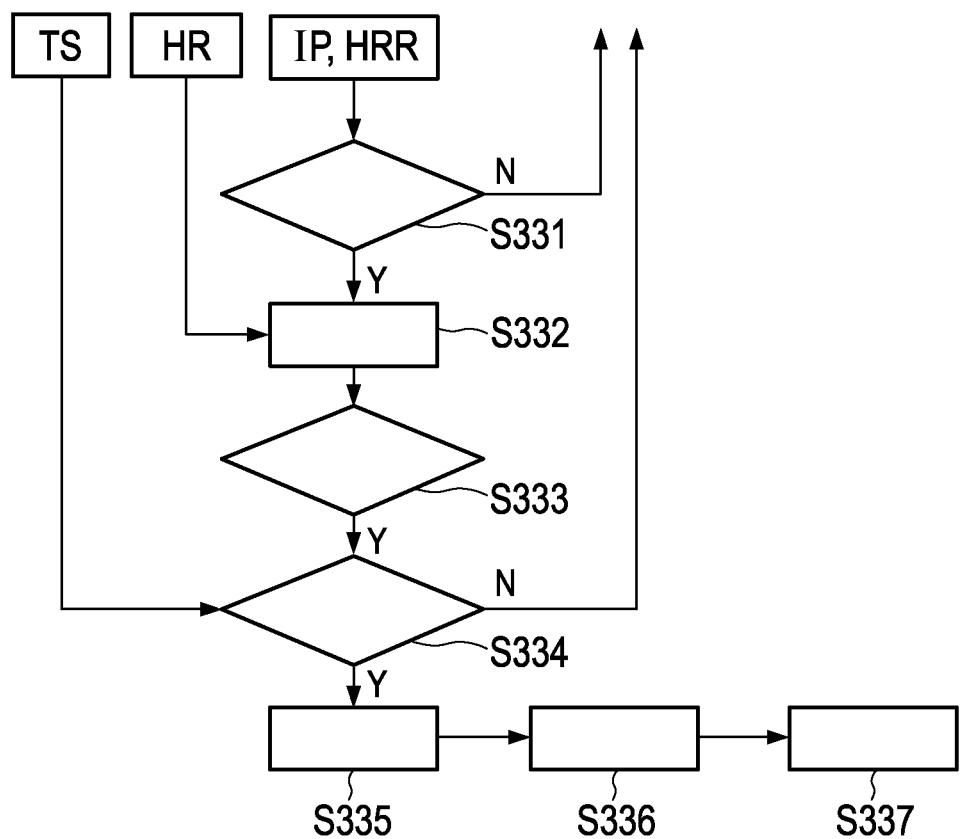
FIG. 5 shows a flow chart indicating an estimation of the resting heart rate by a heart rate monitor system according to an embodiment of the invention.

FIG. 5 shows a flow chart indicating an estimation of the resting heart rate by a heart rate monitor system according to an embodiment of the invention. The resting heart rate calculating unit 330 can receive time stamp information TS, the detected heart rate HR from the heart rate sensor 100 as well as information regarding periods of inactivity IP and/or reliable heart rate data HRR. In step S331, it is determined whether the reliable heart rate data HRR is from periods of inactivity IP or not. If this is not the case, this data is discarded or not considered. In step S332, heart rate data HR is accumulated and the length of the periods of inactivity is determined.

In step S333, it is determined whether the period of inactivity IP is longer than a threshold value which can for example by 5 minutes. In step S334, optionally it is determined whether the periods of inactivity are between 12 am and 7 pm.

If this is the case, then in step S335 the $25^{th}$ percentile of the accumulated heart rate data is calculated as instantaneous estimate of resting heart rate RHRi. From this data, a daily resting heart rate assessment RHRd is determined in step S336. In step S337, a global resting heart rate is determined as an average of for example 5 consecutive days.

Accordingly, in the resting heart rate calculating unit 330, only those reliable heart rate data HRR is considered which occur during periods of inactivity IP which have a duration of at least 5 minutes. All other data is discarded or not considered. Optionally, the periods of inactivity IP can be furthermore restricted, namely to the time period between 12 am and 7 pm. This time period (between 12 am and 7 pm) has a resting heart rate RHR with the lowest deviation from laboratory determined resting heart rates. An instantaneous estimate for the resting heart rate RHRi is determined from the statistical distribution of the heart rate data in the selected periods of inactivity. In step S336, the median of the instantaneous estimates for the resting heart rate is determined for the daily resting heart rate RHR. To further improve the reliability of the resting heart rate, the data from several subsequent days is analyzed.

According to the invention, the heart rate monitor system can be implemented in a wrist device like a smart watch or in a device worn behind the ear of a user. Accordingly, the elements of the heart rate monitor system 10 may be arranged in a single housing. Alternatively, the heart rate sensor 100 can be implemented externally. The same applies to the motion sensor 200. The motion sensor 200 can for example be implemented in a smartphone or mobile device which the user can carry within at all times. Furthermore, the heart rate sensor 100 can also be implemented as an external sensor. The data from the heart rate sensor 100 and the data from the motion sensor 200 can be forwarded to the processing unit 300 wirelessly or by means of wires.

The heart rate sensor 100 can be implemented as any non-invasive sensor which is able to reliably detect a heart rate of a user. Accordingly, the heart rate sensor can be used to sense the electrical, acoustical or optical activity of the heart or the cardio-respiratory system.

According to a preferred aspect of the invention, the heart rate sensor can be embodied as an optical sensor which emits light into a skin of a user and the emitted light is scattered within the skin. Reflected light exits the skin and can be detected by the optical sensor. Accordingly, the optical sensor can be embodied as a photoplethysmography PPG sensor.

The motion sensor 200 can be any sensor which can be used to determine inactive periods of time. Accordingly, the motion sensor can be any sensor which is able to quantify physical activity. This may include a step counter, a GPS sensor for detecting a movement and speed, an indirect cardiometer, a sensor for galvanic skin response or muscle activation. The motion sensor 200 may also be implemented as an activity monitor for determining the activity of a user. Based on these measurements, the periods of inactivity can also be deducted. The motion sensor can for example be used for determining the periodicity of body acceleration, the magnitude of an acceleration, the walking speed, a number of steps per minute or calories burnt during a period of time. Based on this information, a period of inactivity can be determined.

In addition to the above-mentioned operation of the inactivity determining unit 320, the inactivity determining unit 320 may also discard heart rate data from a period of inactivity which immediately follows a period of for example intensive inactivity. During those periods following a period of physical activity, the heart rate HR will still be above the resting heart rate RHR as the body of the user needs to recover. Such a recovery time period $T_{RECOVERY}$ corresponds according to the invention to a period of time in which unreliable heart rate values are detected, wherein this period of time follows a physical activity. The recovery time period $T_{RECOVERY}$ follows the following equation:

$$T_{RECOVERY}=\max(0, T_{MIN}+T_{MAX}\times(\text{median-}(HR_{ACTIVITY})-HR_{LOW})/(HR_{MAX}-HR_{LOW}))$$

Here, $HR_{MAX}$ corresponds to the maximum estimated heart rate according to the age of the user (for example 217−0.85×age). The $HR_{ACTIVITY}$ corresponds to the heart rate detected during periods of physical activity. $HR_{LOW}$ corresponds to the heart rate determined during light physical activity (e. g. $HR_{LOW}$=for example 80 bpm). $T_{MIN}$ corresponds to the minimum recovery time (for example 30 minutes) and $T_{MAX}$ corresponds to the maximum recovery time (for example 120 minutes).

In addition, it should be noted that the time period of inactivity IP from which heart rate data can be extracted to determine a good approximation of the resting heart rate may be different for different people, for different countries etc. According to an aspect of the invention, the processing unit 300 can implement a learning algorithm to determine those periods of time where the most accurate estimation of the resting heart rate can be determined. In particular, only the data from these periods of time can be used to estimate the resting heart rate.

According to an aspect of the invention, the above described elements and units can be implemented in an activity monitor system instead of a heart rate monitor system. Such activity monitor systems are used to give accurate information to the user on his physical activity level, energy expenditure and cardio-respiratory fitness. For such activity monitor systems, the resting heart rate as determined according to the invention is an important parameter.

According to the invention, the heart rate monitor system and in particular the heart rate sensor can be implemented as a wearable sensing device, i.e. a non-invasive sensing device.

A resting heart rate RHR as determined by the processing unit can be outputted to the display or can be outputted to any other external device which may use this information for its own purposes such as accurately detect the physical activity of the user, monitor stress and also for disease prevention.

Other variations of the disclosed embodiments can be understood and effected by those skilled in the art in practicing the claimed invention from a study of the drawings, the disclosure and the appended claims.

In the claims, the word "comprising" does not exclude other elements or steps and the indefinite article "a" or "an" does not exclude a plurality.

A single unit or device may fulfill the function of several items recited in the claims. The mere fact that certain measures are recited in mutually different dependent claims does not indicate that a combination of these measures cannot be used to advantage.

A computer program may be stored/distributed on a suitable medium such as an optical storage means or a solid state medium, supplied together with or as a part of other hardware but may also be distributed in other forms such as via the internet or other wired or wireless telecommunication systems.

Any reference signs in the claims should not be construed as limiting the scope.

The invention claimed is:

1. The heart rate monitor system being implemented as a wearable device, comprising:
   an inactivity determining unit for determining periods of inactivity (IP) of a user based on motion data (MD) detected by at least one motion sensor attached to the user, wherein said motion data comprise one or more of activity counts, speed information, number of step information, and motion level information;
   at least one heart rate sensor for measuring heart rate data (HR) of the user over time and during non-restrictive living conditions;
   a resting heart rate calculating unit for calculating a resting heart rate (RHR) of the user based on said heart rate data (HR) which are measured by the at least one heart rate sensor during the periods of inactivity as determined by the inactivity (IP) determining unit; and
   a reliability establishing unit for establishing reliable heart rate data (HRR) from among the measured heart rate data (HR), wherein the reliability establishing unit ignores heart rate data (HR) which is lower than a lower threshold and heart rate data (HR) which is above an upper threshold; and
   wherein the resting heart rate calculating unit calculates the resting heart rate (RHR) of the user based on the reliable heart rate data (HRR) as established by the reliability establishing unit.

2. The heart rate monitor system according to claim 1, further comprising at least one motion sensor for measuring or determining motion data (MD) of a user over time and during non-restrictive living conditions.

3. The heart rate monitor system according to claim 1, wherein the reliability establishing unit ignores heart rate data (HR) which has a standard deviation which is below a standard deviation threshold.

4. The heart rate monitor system according to claim 3, wherein the lower threshold is 30 beats per minute, the upper threshold is 150 beats per minute and the standard deviation threshold is 0.1 beats per minute.

5. The heart rate monitor system according to claim 1, wherein the inactivity determining unit excludes periods of inactivity (IP) of the user which are not between 12 am and 7 pm.

6. The heart rate monitor system according to claim 5, wherein the resting heart rate calculating unit calculates a resting heart rate (RHR) of the user based on heart rate data (HR) and periods of inactivity (IP) of the user over several days.

7. The heart rate monitor system according to claim 1, wherein the inactivity determining unit determines periods of inactivity (IP) of the user by excluding times of recovery after a physical activity from the determined periods of inactivity (IP).

8. A method of determining a resting heart rate (RHR) of a user using a wearable heart rate monitor system, comprising the steps of:
   determining periods of inactivity (IP) of a user based on motion data (MD) detected by at least one motion sensor of the wearable heart rate monitor system and attached to the user, wherein said motion data comprise one or more of activity counts, speed information, number of step information, and motion level information;

measuring heart rate data (HR) of a user over time and during non-restrictive free-living conditions by a heart rate sensor in the heart rate monitor system; and establishing a reliable heart rate data (HRR) from among the determined or measured heart rate data (HR) by ignoring heart rate data (HR) which is lower than a lower threshold and heart rate data (HR) which is above an upper threshold;

calculating a resting heart rate (RHR) of the user based on the heart rate data (HR) measured during determined periods of inactivity and the reliable heart rate data (RHR).

9. The method of claim 8, further comprising determining motion data (MD) of a user over time and during non-restrictive living conditions based on a motion detector.

10. The method of claim 8, wherein the step of establishing a reliable heart rate data ignores heart rate data (HR) which has a standard deviation which is below a standard deviation threshold.

11. The method of claim 10 wherein the lower threshold is 30 beats per minute, the upper threshold is 150 beats per minute and the standard deviation threshold is 0.1 beats per minute.

12. The method of claim 8, wherein the step of determining periods of inactivity excludes periods of inactivity (IP) of the user which are not between 12 am and 7 pm.

13. The method of claim 12, wherein the step of calculating a resting hear rate comprises calculating a resting heart rate (RHR) of the user based on heart rate data (HR) and periods of inactivity (IP) of the user over several days.

14. The method of claim 8, wherein the step of determining periods of inactivity comprises determining periods of inactivity (IP) of the user by excluding times of recovery after a physical activity from the determined periods of inactivity (IP).

15. A non-transitory machine-readable storage medium encoded with instructions for execution by a processor for monitoring a heart rate of a user in a heart rate monitor system, the non-transitory machine-readable storage medium comprising:

instructions for determining periods of inactivity (IP) of a user based on motion data (MD) detected by at least one motion sensor of the wearable heart rate monitor system and attached to the user, wherein said motion data comprise one or more of activity counts, speed information, number of step information, and motion level information;

instructions for measuring heart rate data (HR) of a user over time and during non-restrictive free-living conditions by a heart rate sensor in the heart rate monitor system;

instructions for establishing a reliable heart rate data (HRR) from among the determined or measured heart rate data (HR) by ignoring heart rate data (HR) which is lower than a lower threshold and heart rate data (HR which is above an upper threshold; and instructions for calculating a resting heart rate (RHR) of the user based on the heart rate data (HR) measured during determined periods of inactivity and the reliable heart rate data (RHR).

16. The non-transitory machine-readable storage medium of claim 15, further comprising instructions for determining motion data (MD) of a user over time and during non-restrictive living conditions based on a motion detector.

17. The non-transitory machine-readable storage medium of claim 15, wherein the instructions for establishing a reliable heart rate data ignore heart rate data (HR) which has a standard deviation which is below a standard deviation threshold.

18. The non-transitory machine-readable storage medium of claim 15, wherein the instructions for determining periods of inactivity exclude periods of inactivity (IP) of the user which are not between 12 am and 7 pm.

19. The non-transitory machine-readable storage medium of claim 18, wherein the instructions for calculating a resting hear rate comprise instructions for calculating a resting heart rate (RHR) of the user based on heart rate data (HR) and periods of inactivity (IP) of the user over several days.

20. The non-transitory machine-readable storage medium of claim 15, wherein the instructions for determining periods of inactivity comprise instructions for determining periods of inactivity (IP) of the user by excluding times of recovery after a physical activity from the determined periods of inactivity (IP).

* * * * *